(12) United States Patent
Paille et al.

(10) Patent No.: US 9,733,489 B2
(45) Date of Patent: Aug. 15, 2017

(54) METHOD FOR PROVIDING A PERSONALIZED SPECTACLE LENS OPTICAL SYSTEM FOR A WEARER

(71) Applicant: ESSILOR INTERNATIONAL (COMPAGNIE GENERALE D'OPTIQUE), Charenton le Pont (FR)

(72) Inventors: Damien Paille, Charenton le Pont (FR); Sarah Marie, Charenton le Pont (FR); Hélène De Rossi, Charenton le Pont (FR)

(73) Assignee: ESSILOR INTERNATIONAL (COMPAGNIE GENERALE D'OPTIQUE), Charenton le Pont (FR)

( * ) Notice: Subject to any disclaimer, the term of this patent is extended or adjusted under 35 U.S.C. 154(b) by 165 days.

(21) Appl. No.: 14/401,747

(22) PCT Filed: May 30, 2013

(86) PCT No.: PCT/EP2013/061179
§ 371 (c)(1),
(2) Date: Nov. 17, 2014

(87) PCT Pub. No.: WO2013/178740
PCT Pub. Date: Dec. 5, 2013

(65) Prior Publication Data
US 2015/0131056 A1 May 14, 2015

(30) Foreign Application Priority Data
May 30, 2012 (EP) .................................. 12305594

(51) Int. Cl.
*G02C 7/02* (2006.01)
*G02C 7/06* (2006.01)
(Continued)

(52) U.S. Cl.
CPC ................ *G02C 7/027* (2013.01); *A61B 3/02* (2013.01); *A61B 3/024* (2013.01); *A61B 3/028* (2013.01);
(Continued)

(58) Field of Classification Search
CPC ........ G02C 7/027; G02C 7/028; G02C 7/068; G02C 13/005; A61B 3/02; A61B 3/024; A61B 3/028; A61B 3/113
(Continued)

(56) References Cited

U.S. PATENT DOCUMENTS 6,382,789 B1    5/2002  Baudart
2012/0212705 A1* 8/2012  Calixte .................. G02C 7/027
                                                351/159.74

FOREIGN PATENT DOCUMENTS

EP          2 442 171      4/2012
WO     WO 2005/091054     9/2005
(Continued)

OTHER PUBLICATIONS

L.E. Grand, "La Distortion En Optique Du Lunetterie", 5ème année No. 1, Jan. 1956.
(Continued)

*Primary Examiner* — Huy K Mai
(74) *Attorney, Agent, or Firm* — Cozen O'Connor

(57) ABSTRACT

A method for providing a personalized optical system for a wearer wherein the optical system characterizes a spectacle ophthalmic lens comprising the following steps: a) providing a visual performance level (VPL) value of at least one eye of the wearer; b) providing a set of rules linking at least the visual performance level of step a) with at least one optical criterion chosen among one or both of the two following optical criteria groups consisting of central vision optical criterion (CVOC) group and peripheral vision optical
(Continued)

criterion (PVOC) group; c) calculating the physical and geometrical parameters of the personalized optical system or selecting the personalized optical system in an optical systems data base comprising a plurality of optical systems, so that to meet the set of rules of step b) according to the visual performance level data provided in step a).

15 Claims, 10 Drawing Sheets

(51) Int. Cl.
    *A61B 3/02*      (2006.01)
    *A61B 3/024*      (2006.01)
    *A61B 3/028*      (2006.01)
    *A61B 3/18*      (2006.01)
    *G02C 13/00*      (2006.01)

(52) U.S. Cl.
    CPC ............... *A61B 3/18* (2013.01); *G02C 7/02* (2013.01); *G02C 7/028* (2013.01); *G02C 7/068* (2013.01); *G02C 13/005* (2013.01)

(58) Field of Classification Search
    USPC ..... 351/159.42, 159.74, 159.75, 159.76, 224
    See application file for complete search history.

(56) References Cited

FOREIGN PATENT DOCUMENTS

WO    WO 2010/043704    4/2010
WO    WO 2010/076294    7/2010

OTHER PUBLICATIONS

P. Allione, F. Ahsbahs and G. Le Saux, "Application of Optimization in Computer-Aided Ophthalmic Lens Design", SPIE vol. 3737, EUROPTO Conference on Design and Engineering of Optical Systems, Berlin, May 1999.

C. Fauquier, T. Bonnin, C. Miege and E. Roland, "Influence of Combined Power Error and Astigmatism on Visual Acuity", Vision Science and its Applications (VSIA), Santa Fe, NM (USA), Feb. 2-7, 1995.

\* cited by examiner

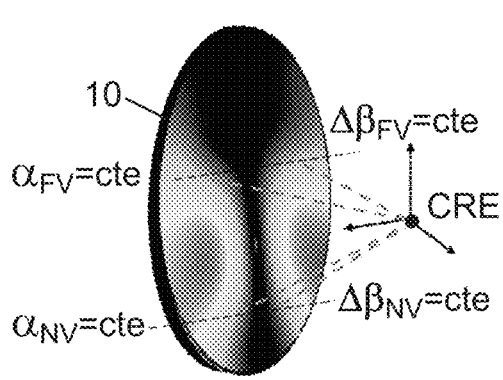
FIG. 11
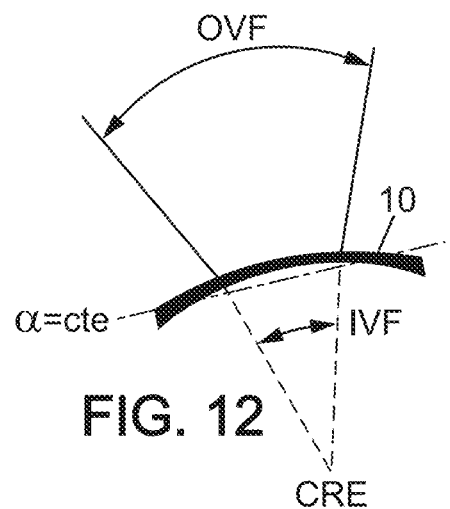
FIG. 12
FIG. 13
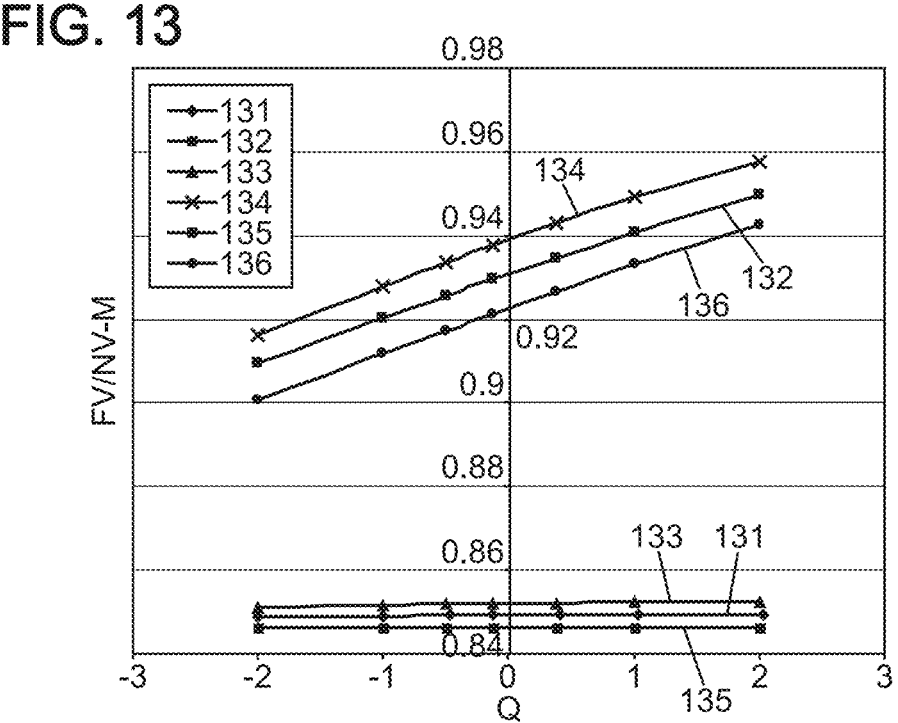

METHOD FOR PROVIDING A PERSONALIZED SPECTACLE LENS OPTICAL SYSTEM FOR A WEARER

RELATED APPLICATIONS

This application is a U.S. National Phase Application under 35 USC 371 of International Application PCT/EP2013/061179 filed May 30, 2013.

This application claims the priority of European application No. 12305594.9 filed May 30, 2012, the entire content of which is hereby incorporated by reference.

FIELD OF THE INVENTION

The invention relates generally to lens adaptation and comfort improvement and more specifically concerns a method for providing a personalized optical system for a wearer by calculating or selecting physical and geometrical parameters of the optical system. According to the present invention the said optical system characterizes an ophthalmic lens ophthalmic lens for said wearer. The ophthalmic lens is meant, without limitation, a spectacle lens (progressive lens, single vision lens, bifocal lens, or trifocal lens . . . ), contact lens, intraocular lenses and the like.

The invention also concerns a method for making a spectacle ophthalmic lens. Furthermore, the invention concerns a piece of software set up for implementing the calculation method for the design of a spectacle ophthalmic lens of the invention.

BACKGROUND OF THE INVENTION

Spectacle ophthalmic lenses are worn and widely used for correcting many different types of vision defects. These include defects such as near-sightedness (myopia) and far-sightedness (hypermetropia), astigmatism, and defects in near-range vision usually associated with aging (presbyopia).

Ophthalmologists or optometrists routinely improve the compensated visual acuity by correcting refractive errors in terms of sphere, cylinder and axis. Said refractive errors are low order aberrations and are known as "prescription data", consisting of sphere, cylinder, axis, addition, and eventually prescribed prism of the prescribed prism value and base orientation determined for a given wearer.

SUMMARY OF THE INVENTION

One object of the invention is to better meet the visual needs of lens users and improve the comfort of lens users, particularly users of progressive lens, and facilitate their adaptation to the lenses.

For this purpose, one aspect of the invention is directed to a method at least partly implemented by computer means for providing a personalized optical system for a wearer wherein the optical system characterizes an ophthalmic lens for said wearer according to his prescription data, the said method comprising the following steps:

a) providing a visual performance level (VPL) value of at least one eye of the wearer, with the provision that prescription data (Rx) consisting of sphere, cylinder, axis, addition, prism are not defined as a visual performance level;

b) providing a set of rules linking at least the visual performance level of step a) with at least one optical criterion chosen among one or both of the two following optical criteria groups consisting of central vision optical criterion (CVOC) group consisting of prismatic deviation in central vision, ocular deviation, object visual field in central vision, image visual field in central vision, magnification in central vision or a variation of preceding criteria;

peripheral vision optical criterion (PVOC) group consisting of pupil field ray deviation, object visual field in peripheral vision, image visual field in peripheral vision, prismatic deviation in peripheral vision, magnification in peripheral vision, or a variation of preceding criteria;

c) calculating by computer means the physical and geometrical parameters of the personalized optical system that meets the prescription data of the wearer or selecting the personalized optical system in an optical systems data base comprising a plurality of optical systems that meet the prescription data of the wearer, so that to meet the set of rules of step b) according to the visual performance level data provided in step a).

In the frame of the present invention, the optical system characterizes, for example but not limited to, a spectacle ophthalmic lens comprising a first and a second surface. The first and/or the second surface of said spectacle lens can be a progressive or a regressive addition surface, a spherical surface, an aspherical surface, a toric surface or an atoric surface.

In the scope of the present invention, the aforementioned terms are understood according to the following definitions:

a "visual performance level" is defined as a performance of an eye that can be measured and considered according to a scale to define a performance level for a wearer. A visual performance level is thus a level of evaluation of a visual system used to quantify the ability of a wearer to detect, to identify and to analyse information coming within his vision field, based on speed, accuracy and quality of his visual perception. A visual performance level may be evaluated thanks to subjective measurements (such as questionnaires) or thanks to objective measurements (such as vision tests). According to the present invention, prescription data, chosen in the list consisting of sphere (optical power suitable for correcting the defect at a given working distance (taken into account during the eye examination), for example, far vision sphere, intermediate vision sphere, near vision sphere (for example the working distance at near is usually 40 cm)), cylinder and axis (astigmatism corrections for an eye of a wearer), addition (dioptric power variation suitable for correcting near vision of an eye of a wearer when far vision is corrected), prescribed prism and base of said prescribed prism are not defined as visual performance levels;

an "optical system" is defined by a set of physical and geometrical parameters; said optical system may be used to further feed lens manufacturing steps;

"physical parameter" represents the intrinsic characteristics of materials that constituting the optical system (refractive index Abbe number, . . . ); the refractive index of materials can be inhomogeneous;

geometrical parameters are parameters used to define the said optical system. Said geometrical parameters may consist for example of coefficients of the equations of the optical system surfaces and the position of each surface relatively to each other. The position of said surfaces relatively to each other can be characterized by offset, rotation, tilt parameters. Resulting local thicknesses are a consequence of the relative positions of the said surfaces. Surfaces of an optical system are usually represented according to a polynomial or parametric equation obtained by using a model based on the B-splines or Zernike polynomials. These models give continuous curvature on the whole surface lens. Surfaces can also be Fresnel or pixelized surfaces. A surface can be a function of several surfaces (for example, the function can be a weighted sum). Locally, at each point of a surface, minimum and maximum curvatures can be defined that derives from the equation of the surface. All the characteristics (such as curvatures) defined using geometrical parameters are also geometrical parameters;

Regarding definitions of said characteristics in conjunction with a spectacle ophthalmic lens:

For each point of the surface, a minimum curvature $CURV_{min}$ is given by the formula:

$$CURV_{min} = \frac{1}{R_{max}}$$

where $R_{max}$ is the local maximum radius of curvature, expressed in meters and $CURV_{min}$ is expressed in diopters.

Similarly, a maximum curvature $CURV_{max}$ can be defined at any point on an aspherical surface by the formula:

$$CURV_{max} = \frac{1}{R_{min}}$$

where $R_{min}$ is the local minimum radius of curvature, expressed in meters and $CURV_{max}$ is expressed in diopters.

It can be noticed that when the surface is locally spherical, the local minimum radius of curvature $R_{mm}$ and the local maximum radius of curvature $R_{max}$ are the same and, accordingly, the minimum and maximum curvatures $CURV_{min}$ and $CURV_{max}$ are also identical.

From these expressions of the minimum and maximum curvatures $CURV_{min}$ and $CURV_{max}$, the minimum and maximum spheres labelled $SPH_{min}$ and $SPH_{max}$ can be deduced according to the kind of surface considered.

When the surface considered is the object side surface—also called front surface, the expressions are the following:

$$SPH_{min} = (n-1)*CURV_{min}$$
$$= \frac{n-1}{R_{max}} \text{ and } SPH_{max}$$
$$= (n-1)*CURV_{max}$$
$$= \frac{n-1}{R_{min}}$$

where n is the index of the constituent material of the lens.

If the surface considered is an eyeball side surface—also called rear surface, the expressions are the following:

$$SPH_{min} = (1-n)*CURV_{min}$$
$$= \frac{1-n}{R_{max}} \text{ and } SPH_{max}$$
$$= (1-n)*CURV_{max}$$
$$= \frac{1-n}{R_{min}}$$

where n is the index of the constituent material of the lens.

As is known, a mean sphere $SPH_{mean}$ at any point on an aspherical surface can also be defined by the formula:

$$SPH_{mean} = \frac{1}{2}(SPH_{min} + SPH_{max})$$

A cylinder CYL is also defined by the formula $CYL=SPH_{max}-SPH_{min}$.

The characteristics of any complex face of the lens may be expressed by means of the local mean spheres and cylinders. A surface can be considered as locally aspherical when the cylinder is at least 0.25 diopters.

The "Base curve" B usually defines the mean sphere of the front surface at a far vision point;

The "addition of a surface" may be defined as the mean sphere variation between the near vision reference point (NV) belonging to the near vision zone and the far vision reference point (FV) belonging to the far vision zone. Reference points can be for instance, but not limited to, control points. The addition of the surface can be expressed as:

$$Add_{surface}=SPH_{mean}(NV)-SPH(FV);$$

If $Add_{surface}>0$, the surface is a progressive surface;

If $Add_{surface}<0$, the surface is a regressive surface. Thus, reference will be made hereafter to "regression values" as being negative values expressed in diopters.

By "regressive surface" is meant a continuous aspheric surface having a far vision zone, a near vision zone and a zone of decreasing mean sphere value connecting the far vision and near vision zones. By "progressive surface" is meant a continuous aspheric surface having a far vision zone, a near vision zone and a zone of increasing mean sphere value connecting the far vision and near vision zones.

Progressive lenses comprise micro-markings that have been made mandatory by a harmonized standard ISO 8990-2. Temporary markings may also be applied on the surface of the lens, indicating positions of control points on the lens, such as a control point for far vision, a control point for near vision; a prism reference point and a fitting cross for instance. If the temporary markings are absents or have been erased, it is always possible to a skilled person to position the control points on the lens by using a mounting chart and the permanent micro-markings.

The micro-markings also make it possible to define referential for both surfaces of the lens.

In a case of a progressive power lens, the lens comprises a far vision zone located in the upper part of the lens, a near vision zone located in the lower part of the lens and an intermediate zone situated in the lower part of the lens between the far vision zone and the near vision zone. The "upper" part of the lens corresponds to a negative lowering angle $\alpha<0°$ and the "lower" part of the lens corresponds to a positive lowering angle $\alpha>0°$. Thus, on the first surface, the "upper" part corresponds to a positive value along the y axis and the "lower" part corresponds to a negative value along the y axis in the frame.

"central vision" (also referred as "foveal vision") describes the perception of the fovea, a small area in the center of the retina that contains a rich collection of cones. In a central vision situation, an observer adjusts its gaze direction to the object in order to hold the retinal image of the object on the fovea. Central vision permits a person to read, watch TV and perform other activities that require fine and sharp vision;

a "gaze direction" is defined by two angles measured with regard to reference axes centered on the center of rotation of the eye;

"peripheral vision" describes the ability to see objects and movement outside of the gaze direction. In a peripheral vision situation, an observer looks in a fixed gaze direction and an object is seen out of this direct line of vision. The direction of a ray coming from the object to the eye is then different from the gaze direction and is referred as peripheral ray direction. Peripheral vision is mainly the perception of the rods, photoreceptor cells located outside the fovea of the retina;

a "peripheral ray direction" is defined by two angles measured with regard to reference axes centered on the eye entrance pupil and moving along the gaze direction axis;

"ocular deviation" is defined in central vision and describes the fact that adding a lens causes an eye to rotate in order to stay focused on the same object. The angle can be measured in prismatic diopters;

"object visual field in central vision" is defined in the object space by the portion of space that the eye can observe scanning an angular portion of the lens determined by at least two gaze directions. For instance, these gaze directions can be defined by the shape of the spectacle frame or by an aberration level that hinders visualizing the object space with a good enough sharpness;

"image visual field in central vision in the image space" is defined for a determined and fixed object visual field in central vision in the object space (eye space), as the angular portion scanned by the eye to visualize the visual field in the object space;

"pupil field ray deviation" describes that a ray coming from an object located in the peripheral field of view is modified by adding a lens on its path to the eye entrance pupil;

"object visual field in peripheral vision" is defined in the object space. It is the portion of space that the eye can observe in the peripheral visual field of view (while the eye is looking in a fixed direction) defined by at least two rays issued from the center of eye entrance pupil. For instance, these rays can be defined by the shape of the spectacle frame or by an aberration level that hinders visualizing the object space with a good enough sharpness;

"image visual field in peripheral vision" is defined for a determined and fixed peripheral object visual field as the corresponding angular portion in the image space viewed by the peripheral vision of the eye;

"prismatic deviation in central vision" is defined in the object space by the angular deviation of a ray issued from the center of rotation of the eye introduced by the quantity of prism of the lens;

"prismatic deviation in peripheral vision" is the angular deviation of a ray issued from the center of the entrance pupil introduced by the quantity of prism of the lens;

"magnification in central/peripheral vision" is defined as the ratio between the apparent angular size (or the solid angle) of an object seen in central/peripheral vision without lens and the apparent angular size (or the solid angle) of an object seen through the lens in central/peripheral vision;

"Distortion" is a defect which is not related to the resolution of images impacting the sharpness or the contrast of the image formed by the periphery of the visual field of the lens but merely to their shape. Distortion can be evaluated in different situations of use of the lens. First, a fixation point is imposed to the wearer so that he keeps his eye immobile (thus the gaze direction is fixed). In this case, the distortion which is evaluated is called static vision, i.e. the direction of gaze is fixed and distortion is analyzed in peripheral vision. Distortion can also be evaluated in dynamic vision, i.e. the direction of gaze is free and distortion is analyzed in central vision.

Static Distortion is due to the variation of preceding criteria with the peripheral ray direction (pupil field ray deviation and/or magnification in peripheral vision). Dynamic Distortion is due to the variation of preceding criteria with the gaze direction (prismatic deviation and/or magnification in central vision).

Evaluation in static or dynamic vision is made depending on the intended use of the lens. Reference can be made to publication <<La distortion en optique de lunetterie>> by Yves LE GRAND Annales d'Optique Oculaire 5ème année No 1 Janvier 1956.

"rules", suitable to link at least a visual performance level with at least one optical criterion, refer to a relationship between the said visual performance level and the said optical criterion.

According to an embodiment, the visual performance level (VPL) of step a) is selected in the list of visual performances levels consisting of a sub-list of visual acuity performances, a sub-list of contrast sensitivity performances, a sub-list of visual space perception performance, a sub-list of reading performance, a sub-list of colour perception performance, a sub-list of self-reported visual performance, or a combination of at least two of said performances. According to the present invention, following wordings refer to further definitions;

"visual acuity performance" refers to acuteness or clearness of vision, which is dependent on the sharpness of the retinal focus within the eye and the sensitivity of the interpretative faculty of the brain;

"contrast sensitivity performance" refers to the difference in visual properties that makes an object (or its representation as an image) distinguishable from other objects and the background. In visual perception, contrast is determined by the difference in the color and brightness of the object and other objects within the same field of view;

"visual space perception" refers to the ability of humans to become aware of the relative position of their own bodies and objects around them. Vision provides cues, such as depth and distance that are important for movement and orientation relative to the environment;

"reading performance" refers to the ability of looking at and interpreting letters or other information that is written;

"color perception performance" refers to the ability to distinguish objects based on the wavelengths (or frequencies) of the light;

"self-reported visual performance" refers to the evaluation by a person of the perceived visual performance in a global way or for different activities and/or different lighting conditions.

According to embodiments of the invention:

the sub-list of visual acuity performances consists of central visual acuity, peripheral visual acuity, dynamic visual acuity, each of said visual acuity being measured either according to monocular or to binocular vision and to either photopic or mesopic or scotopic vision conditions, or a combination of at least two of said visual acuity performances; and/or the sub-list of contrast sensitivity performances consists of spatial contrast sensitivity, time contrast sensitivity, or a combination of said contrast sensitivity performances measured either according to monocular or to binocular vision and to either photopic or mesopic or scotopic vision conditions; and/or the sub-list of "visual space perception" performances consists of distance perception acuteness, stereo acuity, aniseikonia measurement, moving object speed perception, visual field, being measured either photopic or mesopic or scotopic vision conditions, or a combination of at least two of said space perception performances; and/or the sub-list of "reading performances" consists of reading rate performance, reading comprehension performance, word identification performance, being measured either according to monocular or to binocular vision and to either photopic or mesopic or scotopic vision conditions, or a combination of at least two of said reading performances; and/or the sub-list of "color perception performances" consists of hue discrimination, saturation discrimination, brightness discrimination Measured either according to monocular or to binocular vision and to either photopic or mesopic or scotopic vision conditions, or a combination at least two of said color perception performances; and/or the sub-list of "self-reported visual performances" consists of visual related quality of life questionnaires as National Eye Institute (NEI) Visual Functioning Questionnaire or developed questionnaire on subjective visual performance during defined activities and/or defined conditions or a unique question about self-reported visual performances.

According to an embodiment at least two visual performance levels are selected and a global visual performance scale is defined.

According to an example of preceding embodiment, one can determine an average value for each selected visual performance level and calculate a scaled visual performance level as being the ratio between the visual performance level of a viewer divided by the average value of corresponding visual performance level. One can then define a "global" visual performance level based on at least two different visual performance levels where the global visual performance level is defined as being the mean value of the selected scaled visual performance levels.

According to an example, one considers visual acuity measurements according to far vision and to near vision. If the visual acuity for far vision would 14/10 and the visual acuity for near vision would be 12/10, the global vision acuity would thus be 13/10.

Combinations of visual performance levels so as to define a global visual performance level may be following:

photopic visual acuity and mesopic visual acuity and/or scotopic visual acuity;

contrast sensitivity and photopic visual acuity (for example in far vision);

reading rate performance and reading comprehension performance and visual acuity (for example in near vision);

contrast sensitivity and stereoscopic acuity.

According to an embodiment, the optical system is selected in optical systems data base wherein all the optical systems of the optical systems data base have been calculating previously taking into account at least a same focalisation criterion over an evaluation zone according to at least a gaze direction.

According to an embodiment the physical and geometrical parameters of step c) are calculated by computer means thanks to an optimization method wherein at least a focalisation criterion (a) over an evaluation zone according to at least a gaze direction is taken into account to implement the calculation. A focalisation criterion aims at improving optical quality of the image caused by optical aberrations that induce blurring in the image, drop in contrast and causing therefore unclear vision.

Optimization methods are commonly used in the field of ophthalmic lens design.

These methods are known by the one skilled in the art, for example in the publication "*Application of optimization in computer-aided ophthalmic lens design*" (P. Allione, F. Ahsbahs and G. Le Saux, in SPIE Vol. 3737, EUROPTO Conference on Design and Engineering of Optical Systems, Berlin, May 1999), which is incorporated by reference in the present document. Examples of optimization methods are also disclosed in patent literature, such as in U.S. Pat. No. 6,382,789, WO 2010/043704, WO2010/076294.

According to an embodiment the focalisation criterion is selected in the list consisting of optical power, astigmatism, High Order Aberration, Strehl ratio, Root Means Square (RMS), drop in acuity or contrast. For example, the drop in acuity or contrast can be estimated from models taking into account central vision criteria, as power error or astigmatism such as disclosed in FAUQUIER C., BONNIN T., MIEGE C., ROLAND E.: Influence of Combined Power Error and Astigmatism on Visual Acuity, Vision Science and its applications (VSIA), Santa Fe N. Mex. (USA), 2-7 fév. 1995".

According to an embodiment of the invention the personalized optical system characterizing in a progressive addition spectacle lens wherein the front and the back surfaces may be progressive or regressive addition surfaces and wherein the geometrical factor $Q=ADD_F/ADD$ is a parameter used to meet the set of rules of step b) according to step c); $ADD_F$ being the addition of the front surface and ADD being the optical addition of the lens.

According to another embodiment the personalized optical system characterises a progressive addition spectacle lens and wherein the "base curve" of the spectacle ophthalmic lens is a parameter used to meet the set of rules of step b) according to step c).

According to still another embodiment the personalized optical system characterises a progressive addition spectacle lens and wherein refractive index is a physical parameter used to meet the set of rules of step b) according to step c).

According to different embodiments of the present invention, the rules of the set of rules of step b) are chosen within the list consisting of:

providing a desired target value for at least a chosen optical criterion as a function of the value of the visual performance level value of step a);

providing an equality or an inequality equation or a relationship between target values of the same optical criteria evaluated over at least two evaluation zones as a function of the value of the visual performance level value of step a);

providing a trend relationship between at least two chosen optical criteria as a function of the value of the visual performance level value of step a).

According to the present invention:

an "evaluation zone" is associated with a local criterion to be evaluated; it is composed of one or several evaluation domains. An evaluation domain is composed of one or several gaze directions for a criterion belonging to the central vision optical criteria (CVOC) group or to the geometrical local criteria group and of one or several peripheral ray directions for a criterion belonging to the peripheral vision optical criteria group (PVOC);

a "target value" is a value to be reached by a criterion. When the selected criterion is a local criterion, a target value is associated to an evaluation domain. When the selected criterion is a global criterion, a target value is associated to the whole optical system.

According to an embodiment of the present invention:

the visual performance level of step a) is chosen in the sub-list of visual acuity performance, and an optical criterion of step b) is chosen within the visual field list consisting of object visual field in central vision, image visual field in central vision, object visual field in peripheral vision, image visual field in peripheral vision and another optical criterion of step b) is chosen within the magnification list consisting of magnification in central vision, magnification in peripheral vision, and the rule linking the preceding visual performance level and the two preceding optical criteria is a trend relationship where the higher is the visual acuity performance level of the eye of the wearer, the higher is the value of the optical criterion chosen in the visual field list and respectively the lower is the visual acuity performance level of the eye of the wearer, the higher is the value of the optical criterion chosen in the magnification list.

The invention is also directed to a method for manufacturing a spectacle ophthalmic lens for a wearer, the method comprising the following steps:

aa) providing the physical and geometrical parameters of a personalized optical system according to any of preceding claims;

bb) providing a lens substrate;

cc) manufacturing the spectacle ophthalmic lens according to the parameters of step aa).

The invention is also directed to a computer program product comprising one or more stored sequence of instruction that is accessible to a processor and which, when executed by the processor, causes the processor to carry out the step c) of present invention and optionally the other steps of any of here above mentioned embodiments.

The invention is also directed to a computer-readable medium carrying one or more sequences of instructions of the preceding computer program product(s).

Unless specifically stated otherwise, as apparent from the following discussions, it is appreciated that throughout the specification discussions utilizing terms such as "computing", "calculating" "generating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

BRIEF DESCRIPTION OF THE DRAWINGS

FIGS. 11 to 17 relate to a second embodiment according to the present invention.

DETAILED DESCRIPTION OF THE DRAWINGS

Skilled artisans appreciate that elements in the figures are illustrated for simplicity and clarity and have not necessarily been drawn to scale. For example, the dimensions of some of the elements in the figures may be exaggerated relative to other elements to help improve the understanding of the embodiments of the present invention. Same reference on different figures refers to the same object.

Figure 1:
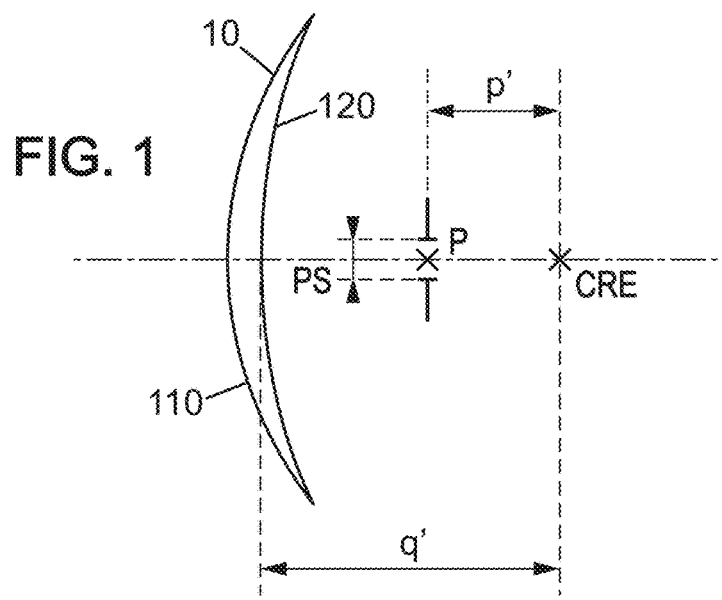
FIG. 1 shows a schematic view of a lens plus eye system.

FIG. 1 illustrates a schematic view of a lens-plus-eye system. The lens 10 has a front face 110 and a rear (or back) face 120. Referring to FIG. 1, an eye position can be defined by the center of rotation of the eye, CRE, and the entrance pupil central point P. PS is the pupil size (not drawn to scale). The distance q' between the CRE and the lens 10 is generally, but not limited to, set to 25.5 mm, and p' defines the position of the eye entrance pupil with respect to the CRE.

Figure 2:
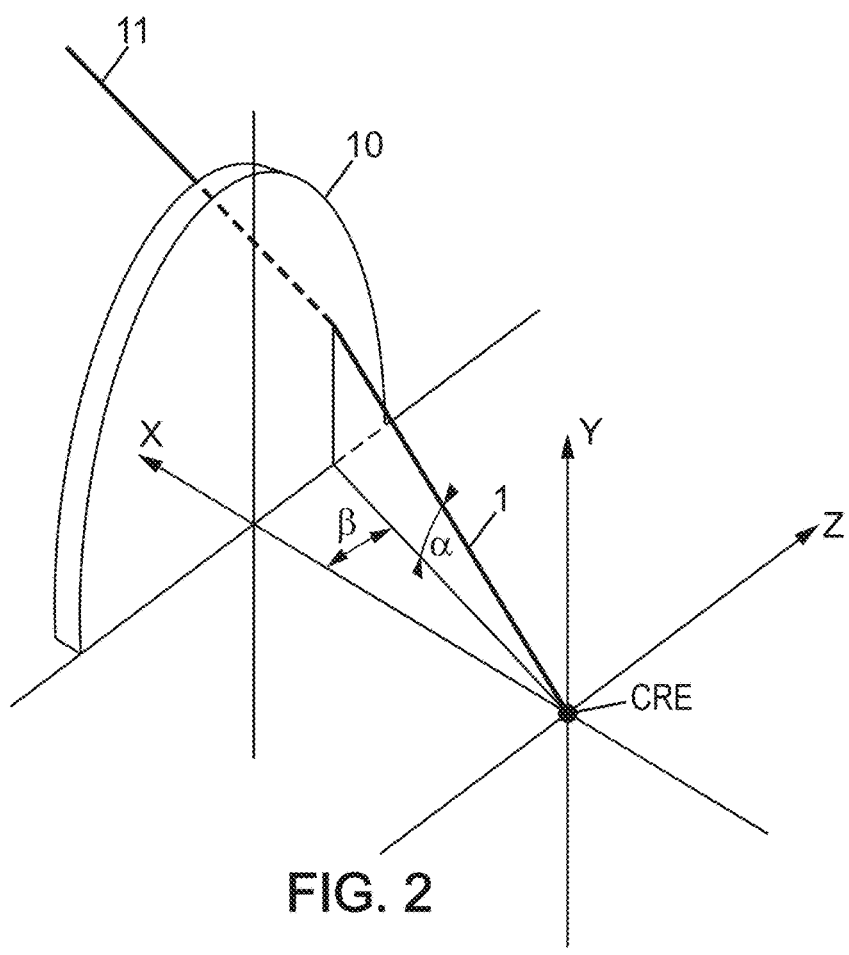
FIG. 2 shows a ray tracing from the center of rotation of the eye.

FIG. 2 illustrates a model for central vision in the purpose of assessing a criterion in a central vision situation by ray tracing. In a central vision situation, the eye rotates about its center of rotation as well as the entrance pupil of the eye. A gaze direction is defined by two angles $(\alpha, \beta)$ measured with regard to reference axes R=(X,Y,Z) centered on the CRE. For assessing a central vision criterion in a gaze direction (α,β), a gaze ray 1 is built from the CRE in the gaze direction (α,β). 11 is the incident ray after passing through the lens 10.

Figure 3:
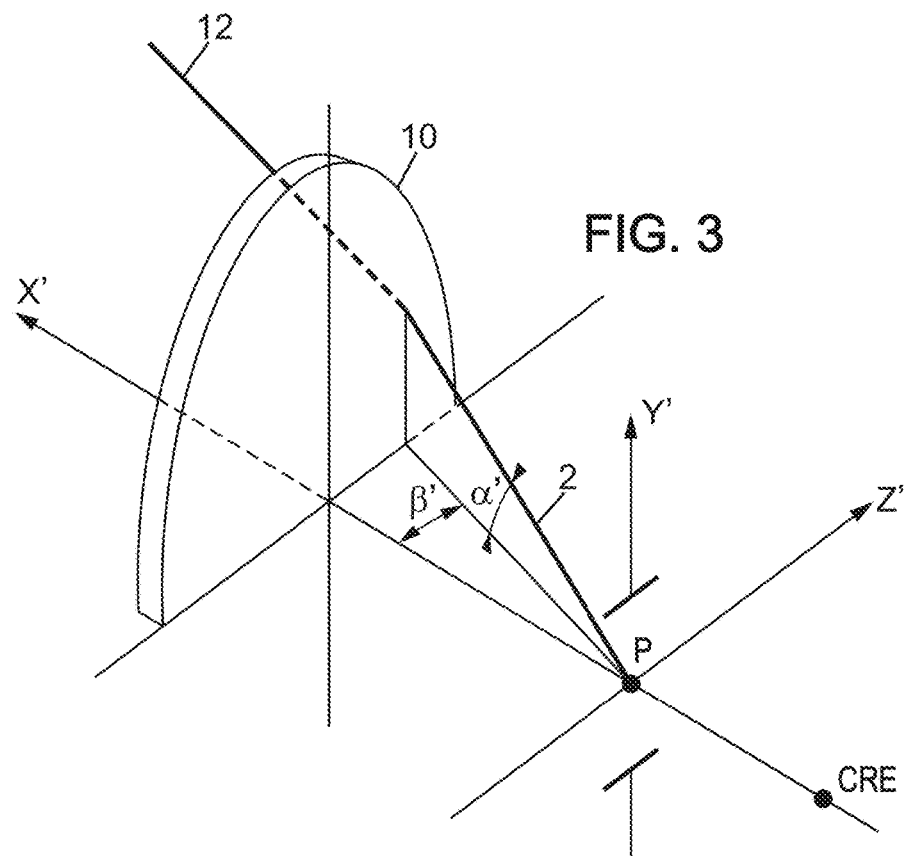
FIG. 3 shows a ray tracing from the center of the eye entrance pupil.

FIG. 3 illustrates a model for peripheral vision in the purpose of assessing a criterion in a peripheral vision situation through ray tracing. In a peripheral vision situation, a gaze direction (α,β) (not represented here) is fixed, and an object is viewed in a peripheral ray direction different from the gaze direction. A peripheral ray direction is defined by two angles (α',β') measured with regard to reference axes R'=(X',Y',Z') centered on the eye entrance pupil and moving along the gaze direction axis given by the fixed direction (α,β) and represented by axis X' on FIG. 3. For assessing a peripheral vision criterion in a peripheral ray direction (α',β'), a peripheral ray 2 is built from the center of the pupil P in a peripheral ray direction (α',β'). 12 is the emergent peripheral ray corresponding to the incident peripheral ray 10.

According to the gaze ray 1 (in central vision) or to the peripheral ray 2 (in peripheral vision), the ray-tracing software computes the corresponding emergent ray, alternatively under reference 11 and 12 on FIGS. 2 and 3. Then, an object point is chosen on the ray in the object space and from this object a pencil of rays is built to calculate the final image. Ray tracing enables then to compute the selected criteria.

Figure 4:
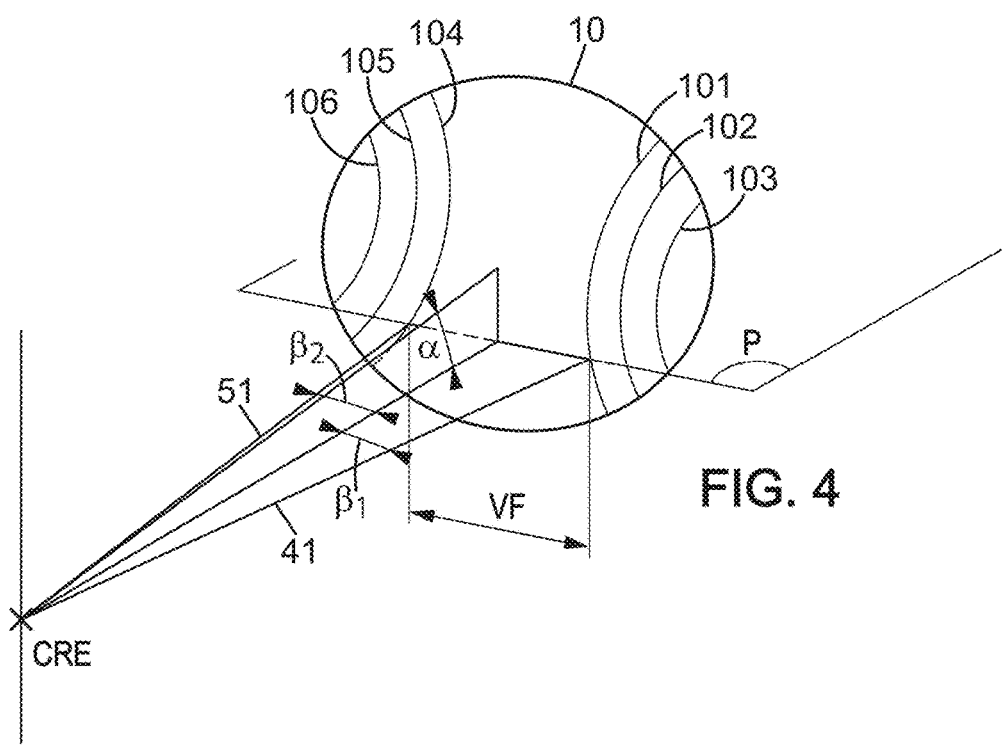
FIG. 4 illustrates horizontal object visual field.

FIG. 4 illustrates an example of visual field VF in central vision for two rays 41 and 51 issued from the CRE. The lens 10 is represented as a surface with isoastigmatism lines 101-106. Rays 41 and 51 are defined as the intersection between a predetermined horizontal axis given by a direction α and two predetermined isoastigmatism lines 101 and 104. These intersections enable to trace ray 41 along direction (α,β1) and ray 51 along direction (α,β2). The object visual field VF in central vision is a function of prismatic deviation and can be mathematically expressed for two rays as:

$$VF(\alpha) = |\beta1 + Dp\_H(\alpha,\beta1)| + |\beta2 + Dp\_H(\alpha,\beta2)|$$

Dp_H(α,β1) represents horizontal prismatic deviation in the gaze direction (α,β1). Horizontal prismatic deviation is the component of the prismatic deviation in a horizontal plane.

Dp_H(α,β2) represents horizontal prismatic deviation in the gaze direction (α,β2).

Figure 5A:
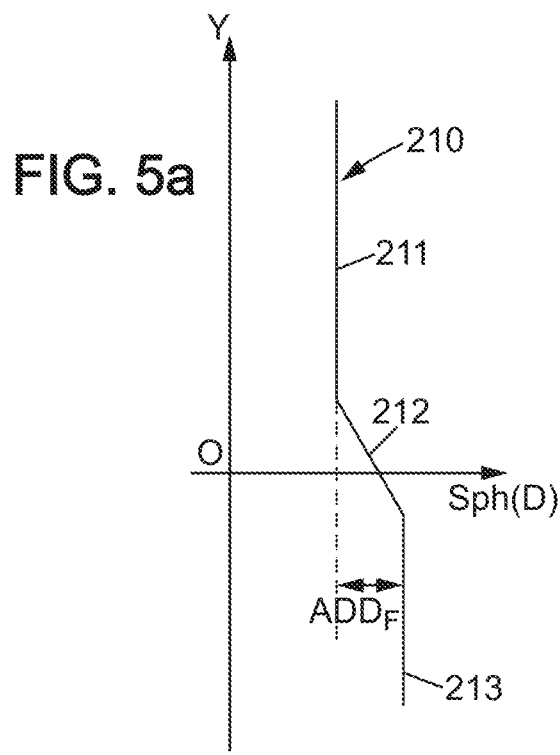
FIGS. 5a and b illustrate addition of a surface.

FIGS. 5a and b illustrate addition of respectively the front surface (for example reference 110 of FIG. 1) and of the back surface (120 of FIG. e1) of a progressive addition spectacle ophthalmic lens, where the variation of the sphere value Sph (in diopter) (respectively 210, 220) is represented according to the Y axis.

Zones 211, 221 regard the far vision zones, zones 213, 223 regard the near vision zones and zones 212, 222 regard the intermediate vision zone. Addition, $ADD_F$, respectively $ADD_B$, refer to the sphere value difference between the near vision zone and the far vision zone when considering the front surface and respectively to the sphere value difference between the far vision zone and the near vision zone when considering the back surface.

Figure 5B:
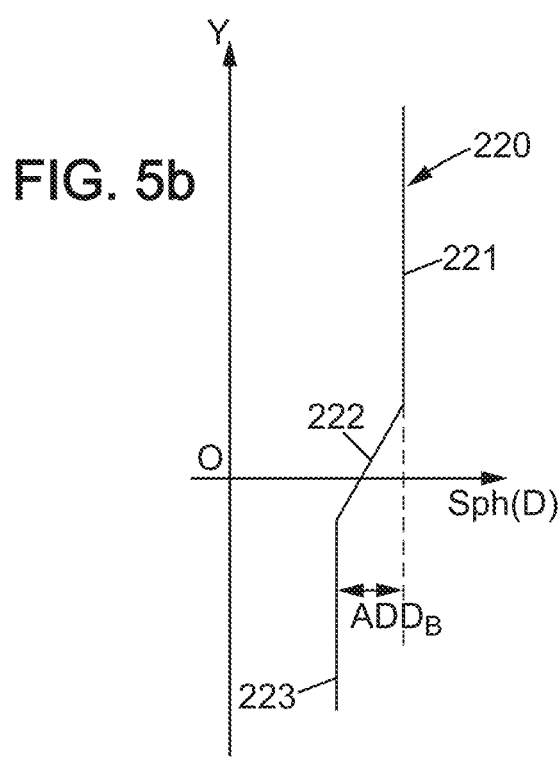

According to the examples of FIGS. 5a and 5b both front and back surfaces are progressive surfaces and the resulting addition of a lens having said both surfaces would be about $ADD = ADD_F + ADD_B$.

According to the present invention a parameter Q is defined where $Q = ADD_F/ADD$.

FIGS. 6 to 10 relate to a first example of an embodiment of the method according to the present invention.

According to this example, the visual performance level of step a) of the method of the invention is the central visual acuity measured according to binocular vision and two optical criteria of step b) of the method of the invention are chosen directed to object visual field in central vision and to magnification in central vision.

According to said example, the object visual field in central vision is considered in the near vision zone.

Figure 6:
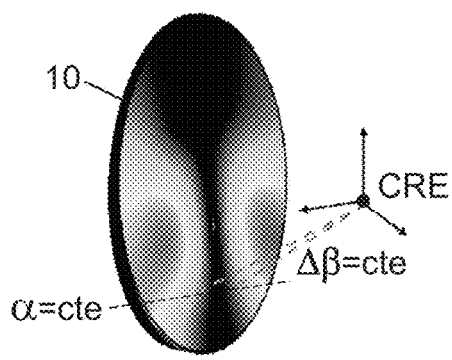
FIGS. 6 to 10 relate to a first embodiment according to the present invention.
Figure 7:
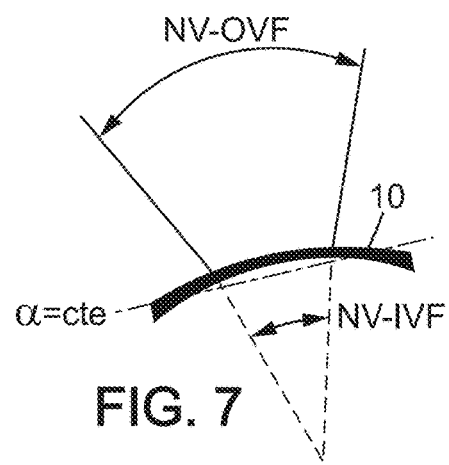

FIGS. 6 and 7 show how said parameter is evaluated; the field to be considered refers to a field which incorporates rays passing through the CRE in directions defined for a given α value and for a β range Δβ.

α is chosen so as the rays passing through the CRE meet the near vision zone. For said example, α=−34°, and Δβ=20° for a central β value of 6° (thus β ranges from −4° to +16°).

The vision field situated between the CRE and lens 10 is the near vision image vision field (NV-IVF), equal to Δβ and the vision field seen after passing through lens 10 is the near vision object vision field (NV-OVF).

For the purpose of the demonstration, one chooses a lens 10 which fits a prescription where the prescribed dioptric power in far vision is −3 diopters, the prescribed astigmatism is 0 in far vision and the addition is +2 diopters.

One further considers the case where Q, the ratio of the repartition of the addition between the front and the back surfaces, is a parameter used to meet a set of rules of step b) according to step c) of the method of the invention.

Figure 8:
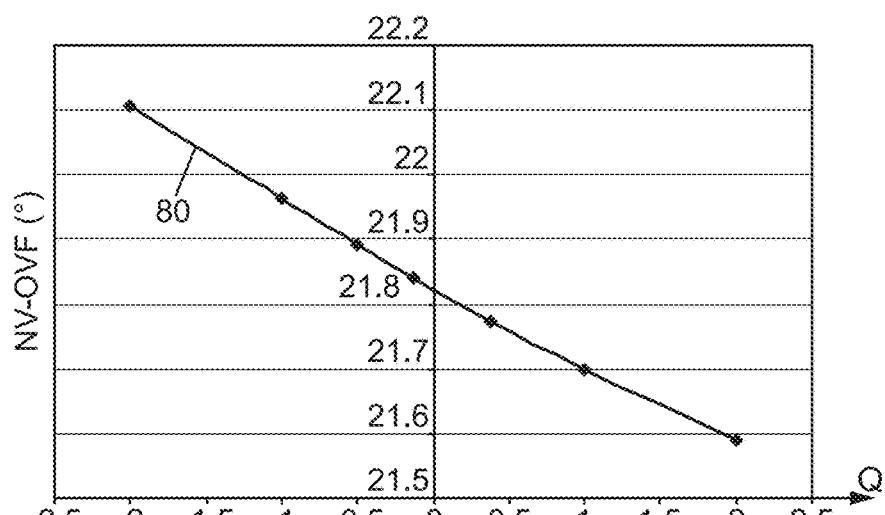
Figure 9:
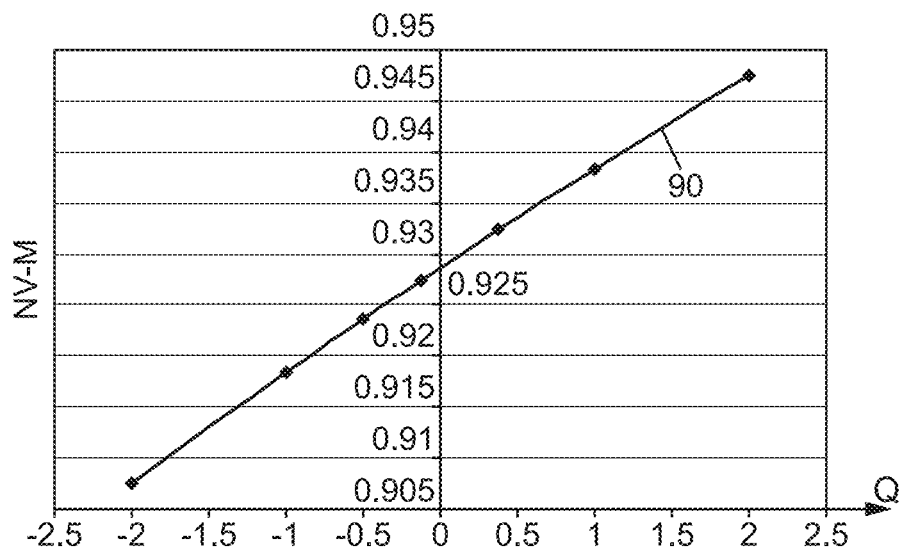
Figure 10:
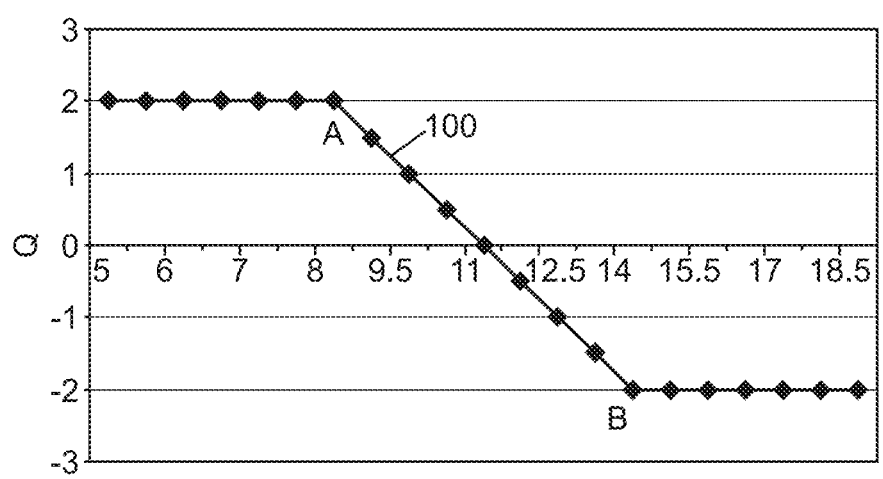

A plurality of ophthalmic lens optical systems has been evaluated and results are reported on FIGS. 8 to 10 where:

In FIG. 8, curve 80 corresponds to the variation of NV-OVF as a function of Q for NV-IVF constant;

In FIG. 9, curve 90 corresponds to the variation of the near vision magnification, NV-M, as a function of Q.

In FIG. 10, curve 100 corresponds to Q variation as a function of central visual acuity measured according to binocular vision.

Values presented in those figures relate to optical system characteristics that have been calculated by computer means thanks to an optimization method wherein at least a focalisation criterion over an evaluation zone according to at least a gaze direction is taken into account to implement the calculation.

The calculated optical systems of the example have been obtained thanks to following steps:

performance definitions of optical system targets where, for each gaze direction within a 40° vision cone, performances are defined regarding focalisation criteria consisting of optical power and astigmatism (meaning that for each gaze direction an optical power and an astigmatism values are attributed);

optimization where the generated optical systems have a variable addition between the front and the back faces (Q variation), but are calculated so as the optical performances are substantially the same regarding optical power and astigmatism values; therefore in each gaze direction the calculation is done so that the tolerance regarding optical power value is equal or less than 0.05 diopters and regarding the astigmatism value is equal or less than 0.1 diopters; according to said calculations, the optical power and astigmatism values of the different optical systems are substantially the same, but criteria regarding visual field and magnification may vary from an optical system to another one.

Results of said calculations are presented on FIGS. 8 to 10.

FIG. 8 shows the variation of the calculated near vision object visual field (NV-OVF, in degrees) according to the Q factor.

FIG. 9 shows the variation of the calculated near vision magnification according to the Q factor.

Said curves demonstrate that NV-OVF and NV-M vary according to opposite trends as a function of the Q factor.

FIGS. 8 and 9 demonstrate that one can offer ophthalmic spectacle lens optical systems where the optical performance regarding optical power and astigmatism values are substantially the same, but where visual field and magnification may significantly vary.

Thanks to variation of visual field and magnification for given optical power and astigmatism values, one can provide optical system suitable to meet the needs of a specific wearer.

Said needs can be linked to a visual performance level of the wearer.

Therefore and according to the present invention, one proposes to improve the visual comfort of the wearer thanks to increasing the magnification value (near vision magnification according to the present example) when the wearer's acuity is low so that the wearer can more easily take into account object image details; one also proposes to improve the visual comfort of the wearer thanks to enlarging his vision field (near vision object visual field according to the present example) when the wearer's acuity is high so that the wearer can more easily scan his environment.

According to the present example, said balance between vision field and magnification can be obtained thanks to varying the repartition of the addition between the front and the back surface (Q factor). Thus the Q factor can be chosen as a parameter used to meet the set of rules of step b) according to step c) of the process according to the invention.

An example of a said rule is illustrated in FIG. 10 where the chosen Q factor (ordinate) is determined as a function of the maximal corrected central vision acuity measured according to binocular vision (abscissa).

For wearers which acuity is low (equal or less than 8/10), one suggests to choose a Q factor equal to 2, meaning that, according to FIGS. 8 and 9, a high NV-M value is preferred and according to the present example NV-OVF=21.6° and NV-M=0.95.

For wearers whose acuity is high (equal or more than 14/10), one suggests to choose a Q factor equal to −2 meaning that a high NV-OVF value is preferred, and according to the present example NV-OVF=22.10° and NV-M=0.91.

For wearers whose acuity is medium, one suggests to find a compromise between the two said optical parameters where the Q factor varies linearly between the two preceding values. Thus and according to the present example, one choose Q=−1 for an intermediate acuity equal to 12.5/10 thus NV-OVF=22.0° and NV-M=0.92. According to a second example of the method according to the present invention, one aims to obtain optimized optical systems when considering both far vision and near vision.

Evaluation zones are defined according to FIGS. 11 and 12, both for far vision and near vision zones. According to the present example $\Delta\beta_{NV}=\Delta\beta_{FV}=20°$ centered around $\beta=6°$ for $\beta_{NV}$ and centered around $\beta=0°$ for $\beta_{FV}$.

$\alpha$ values are following: $\alpha_{NV}=34°$ and $\alpha_{FV}=-8°$.

Optimisation process is implemented according to the rules described regarding the preceding example.

For the present example the prescription of the wearer is sphere −3 in far vision, the astigmatism is 0 in far vision and the addition is 2.

Figure 14:
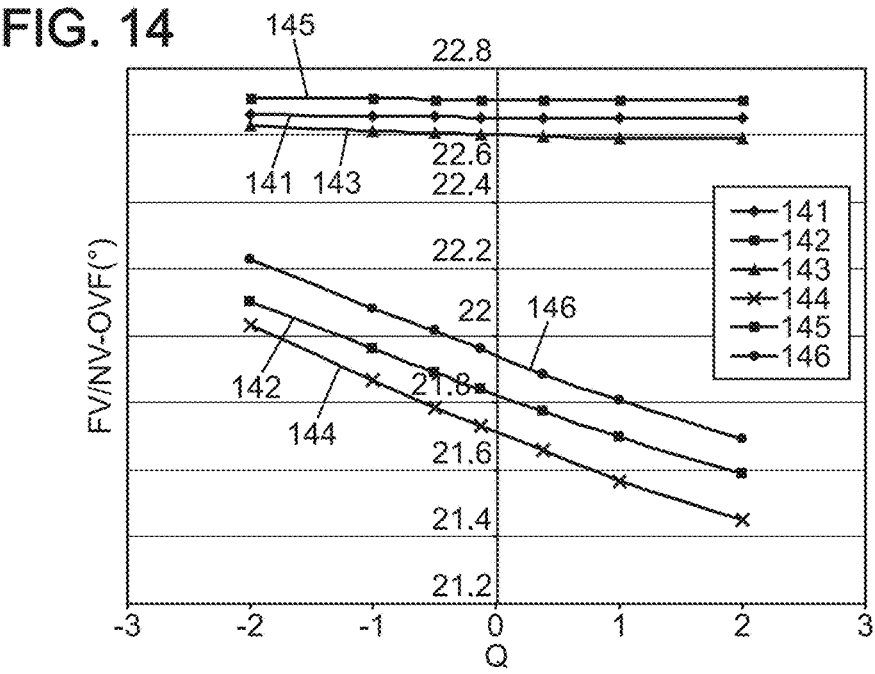

FIGS. 13 and 14 show the variation of respectively magnification parameters and object visual field parameters according to the Q factor and to the base curve B of the optical system.

FIG. 13 shows calculated curves regarding magnification parameters as referred in table 1 where the number of the curve is defined according to the base curve B and to the vision zone.

TABLE 1

| Base curve B (in diopter) | Near vision NV-M (number of the curve) | Far vision FV-M (number of the curve) |
| --- | --- | --- |
| 1.75 | 136 | 135 |
| 2.75 | 132 | 131 |
| 3.75 | 134 | 133 |

FIG. 14 shows calculated curves regarding vision field parameters referred in table 2 where the number of the curve is defined according to the base curve B and to the vision zone.

TABLE 2

| Base curve β (in diopter) | Far vision FV-OVF (number of the curve) | Near vision NV-OVF (number of the curve) |
| --- | --- | --- |
| 1.75 | 145 | 146 |
| 2.75 | 141 | 142 |
| 3.75 | 143 | 144 |

FIG. 13 teaches that far vision or near vision magnification (respectively FV-M and NV-M) vary according to different trends when considering the Q factor and the base curve value.

FV-M and NV-M increase when the base curve value increases, for a constant Q factor value.

The FV-M(Q) curves are almost parallel one to another when the base curve value varies.

Same applies for NV-M(Q).

NV-M values increase, for a same base curve value when the Q factor increases, where FV-M values are almost constant, for a same base curve value, as a function of the Q factor.

FIG. 14 teaches that far vision or near vision object visual field (respectively FV-OVF and NV-OVF) vary according to different trends when considering the Q factor and the base curve value.

FV-OVF and NV-OVF decrease when the base curve value increases, for a constant Q factor value.

The FV-OVF (Q) curves are almost parallel one to another when the base curve value varies.

Same applies for NV-OVF(Q).

NV-OVF values decreases, for a same base curve value when the Q factor increases, where FV-OVF values are almost constant for a same base curve value, as a function of the Q factor.

Thanks to said curves, one can offer to a wearer an optimized optical system when choosing an adapted base curve value and Q factor value according to his visual acuity.

One can make the assumption that the global visual perception of a wearer which visual acuity is more than 14/10 is only limited by object visual field. For such wearers, an optimized solution would be offering an optical system where object visual fields are the largest, both for near and far visions. Thanks to the teachings of FIGS. 13 and 14, one will choose an optical system where the base curve value is 1.75 and the Q factor is −2.

On the opposite side, one can make the assumption that the global visual perception of a wearer which visual acuity is less than 8/10 is only limited by magnification. For such wearers, an optimized solution would be offering an optical system where magnification is the largest, both for near and far vision.

Thanks to the teaching of FIGS. 13 and 14, one will choose an optical system where the base curve is 3.75 and the Q factor is 2.

For wearers which visual acuity is between 8/10 and 14/10, one will suggest different routes taking into account the here above mentioned parameters.

According to an embodiment, one defines two weighting factors, one directed to magnification $F_M$ and the other one directed to object visual field $F_{OVF}$. Each weighing factor, F, varies between 0 and 1.

When considering a range of magnification or object visual field values calculated according to different parameters, such as the base curve value and/or the Q factor value, one will choose an optical system where:

$$M = M_{min} + (M_{max} - M_{min}) \times F_M \text{ and}$$

$$OVF = OVF_{min} + (OVF_{max} - OVF_{min}) \times F_{OVF}$$

where "max" refers to the highest value calculated for magnification, respectively object visual field when varying the parameter(s) within a chosen range and "min" refers to corresponding lowest value.

For wearers which visual acuity is equal or less than 8/10, one will define $F_M=1$ and $F_{OVF}=0$.

For wearers which visual acuity is equal or more than 14/10, one will define $F_M=0$ and $F_{OVF}=1$.

Figure 15:
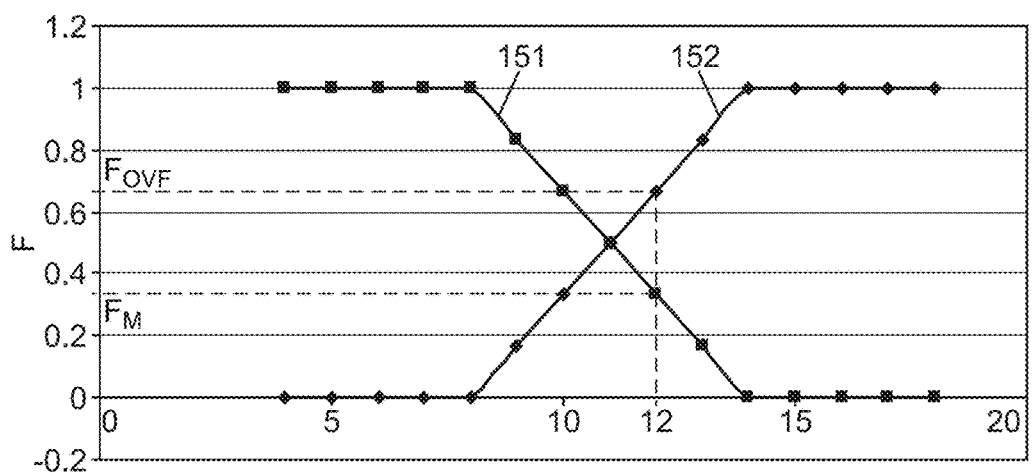

Between said two cases, one will choose a F factor according to FIG. 15 where the abscissa relates to visual acuity and ordinate to the weighing factor F.

Curve 151 represents the variation of $F_{OVF}$ and curve 152 represents the variation of $F_M$, according to visual acuity.

Dotted lines regard an example where the wearer's visual acuity is 12. Thanks to FIG. 15 one determines $F_M=0.33$ and $F_{OVF}=0.67$.

Following values are then determined:
FV-M=0.86
NV-M=0.94
FV-OVF=22.63°
NV-OVF=21.71°

Figure 16:
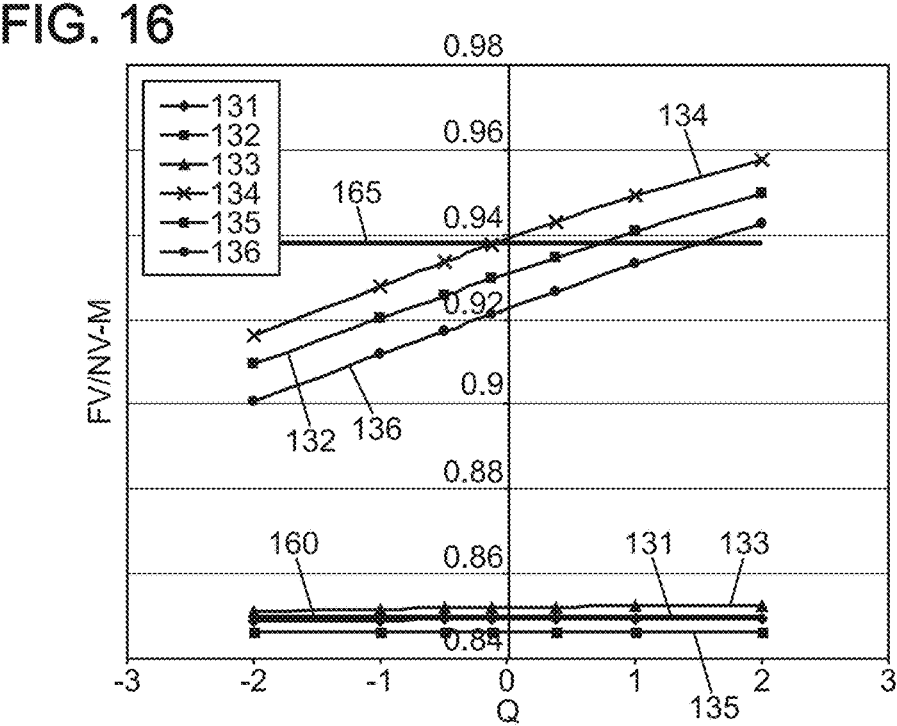
Figure 17:
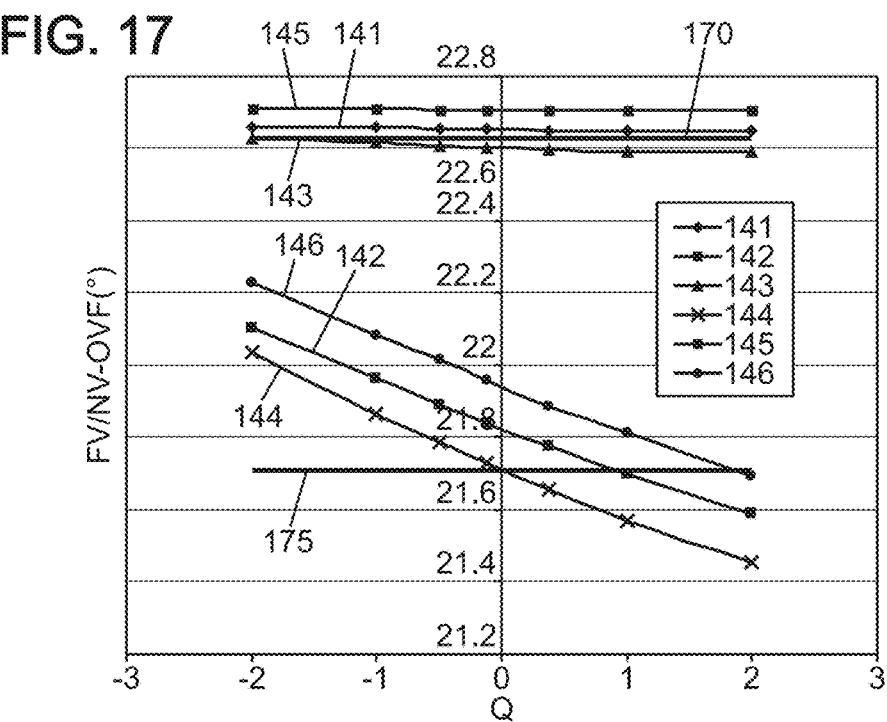

Results are reported on the data of FIGS. 13 and 14 as shown on FIGS. 16 and 17, where one can determine that the best optical system for said wearer relates to a base curve value of 2.75 and a Q factor equal to 1.

Figure 20:
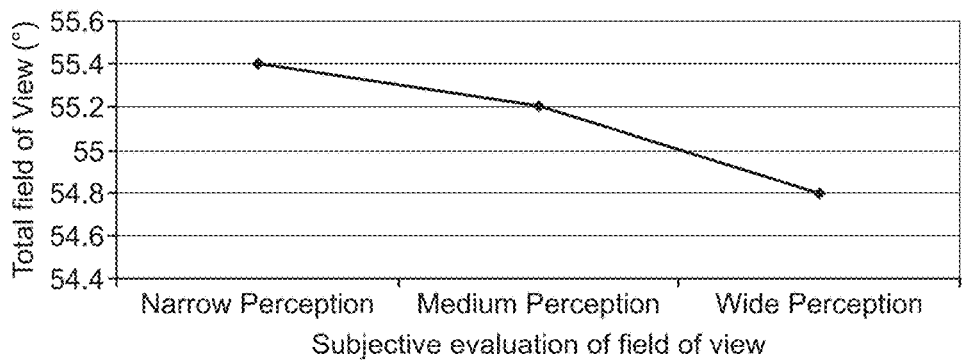
FIG. 20 shows an exemplary embodiment of a rule of step b) linking one visual performance level with one optical criterion, according to the present invention.

FIG. 20 shows an exemplary embodiment of a rule of step b) linking a subjective estimation of the total field of view by a wearer (visual performance level) with the field of view (optical criterion) according to the present invention.

Figure 21:
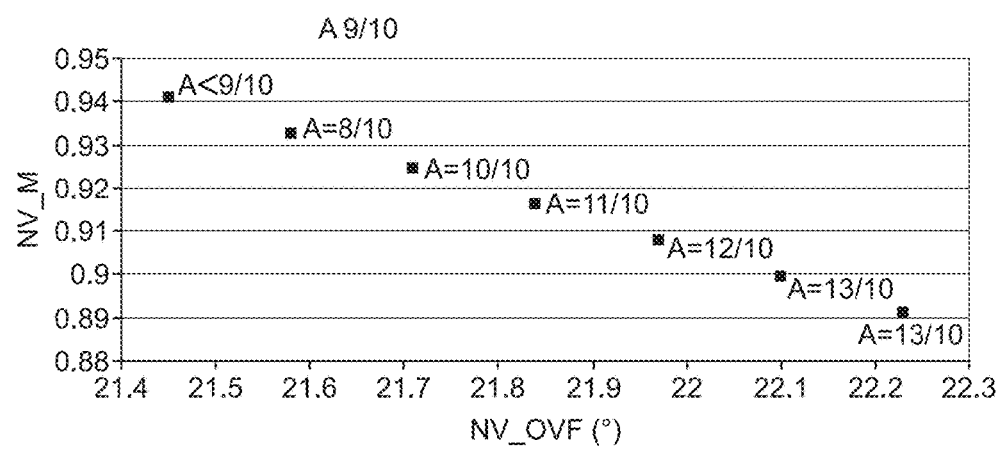
FIG. 21 shows an exemplary embodiment of a rule of step b) linking one visual performance level with two optical criteria, according to the present invention.

FIG. 21 shows an exemplary embodiment of a rule of step b) linking a visual acuity (A) of a wearer with NV-OVF and NV-M, according to the present invention.

This rule is for example set from the graph shown in FIG. 15.

Figure 18:
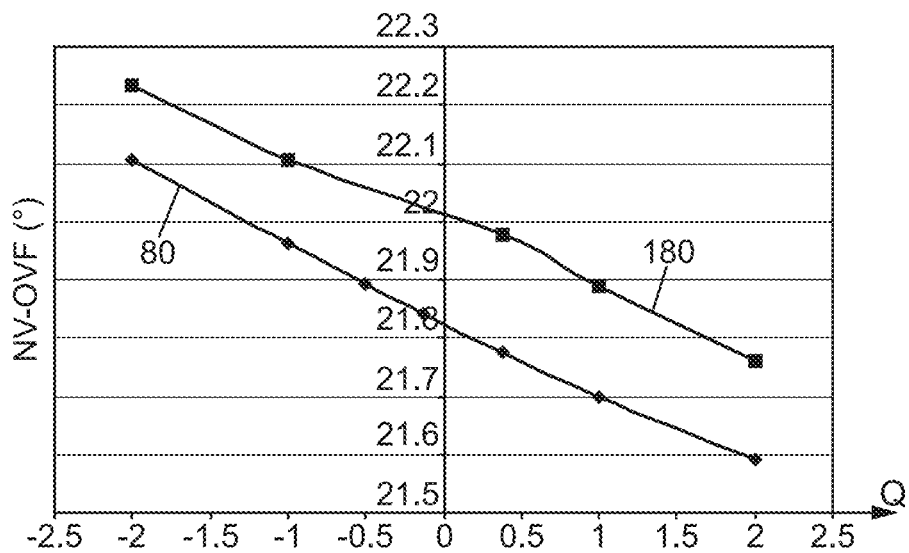
FIGS. 18 and 19 relate to a third embodiment according to the present invention.
Figure 19:
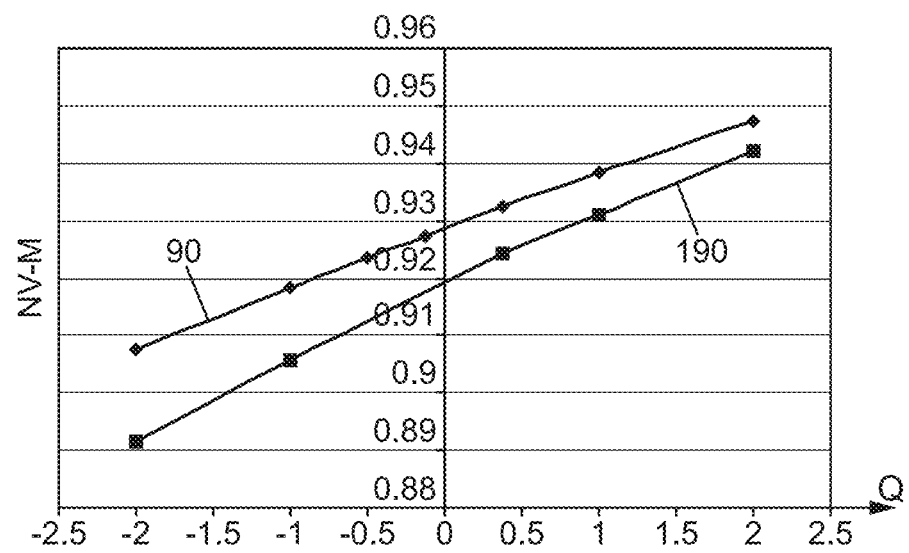

FIGS. 18 and 19 relate to a third example of an embodiment according to the present invention where one aims to offer another approach to the problem addressed according to the first example according to the invention. Then, according to said third example, object visual field in central vision is considered in the near vision zone (as illustrated on FIGS. 6 and 7).

According to said example, one let geometrical parameters of the optical system vary so as to let the Q factor value vary according to visual acuity. Constraints regarding optical power and astigmatism are released to let the optimization according to magnification and object visual field be more efficient.

According to following example, a plurality of wearers have the same prescription, where the prescribed dioptric power in far vision is −3 diopters, the prescribed astigmatism is 0 diopter in far vision, and the addition is 2.

Different optical systems have been evaluated where the Q factor is taken into account according to following steps:

optical system target performances are defined where, for each gaze direction within a vision cone of 40°, performances are specified for optical power and for astigmatism;

optimization is implemented wherein all the generated optical systems have different addition repartition between front and back surfaces (i.e. different Q factor values); optimization is made in each gaze direction so as the tolerance regarding optical power value is equal or less than 0.3 and regarding the astigmatism value is equal or less to 0.3 (said tolerance values were respectively 0.05 and 0.1 according to the first example).

Other steps are similar to those of the first example.

One will then generate a plurality of optical systems which are in the vicinity of those according to the first example but differ because the weight on focalisation criteria (optical power and astigmatism) compared to the weight of optical criteria (object vision field and/or magnification) is lowered in the present example compared to the first example.

Table 3 reports data used to calculate two examples of optical system and corresponding results according to the first example and the third example of embodiments according to the present invention. The optical system is referred as (x, y) where x corresponds to an optical system example and y corresponds to associated Q factor (which is equal to 2 or −2 according to the present optical system examples).

TABLE 3

| Example of embodiment | Optical system | Optical power Target | Optical power Final value | Astigmatism Target | Astigmatism Final value | NV-M final | NV-OVF final (°) |
|---|---|---|---|---|---|---|---|
| 1 | (1, 2) | −0.7 ± 0.05 | −0.68 | 0 ± 0.1 | 0.06 | 0.948 | 21.59 |
| 1 | (2, −2) | −0.7 ± 0.05 | −0.74 | 0 ± 0.1 | 0.1 | 0.908 | 22.10 |
| 3 | (1, 2) | −0.7 ± 0.3 | −0.83 | 0 ± 0.3 | 0.24 | 0.941 | 21.76 |
| 3 | (2, −2) | −0.7 ± 0.3 | −0.97 | 0 ± 0.3 | 0.26 | 0.891 | 22.23 |

FIGS. 18 and 19 show the results according to the first example of an embodiment (results of FIGS. 8 and 9 are reported) compared to those of the present third example of an embodiment of the invention, where near vision object visual field results as a function of the Q factor are reported on FIG. 18 and results of near vision magnification as a function of the Q factor is reported on FIG. 19.

Thanks to releasing tolerances regarding the optical power value and the astigmatism value, one can offer largest object visual fields or highest M for the wearer for the same Q factor value compared to the first example of an embodiment.

One can than offer to a wearer an optimized optical system based on the set of optical systems determined according to said third example of an embodiment and where the selection is made according to the former teaching of the first example of an embodiment of the present invention.

It is clear that it is possible to employ other methods of optimization, and other ways of representing surfaces differing from the method proposed.

The invention has been described above with the aid of embodiments without limitation of the general inventive concept. In particular the present invention provides a method for calculating by optimization an optical system, the optical system being all kinds of optical lenses, particularly ophthalmic lenses, e.g. single vision (spherical, torical), bi-focal, progressive, aspherical lenses (etc.).

The invention claimed is:

1. A method at least partly implemented by computer means for providing a personalized optical system for a wearer wherein the optical system characterizes an ophthalmic lens for said wearer according to his prescription data, the method comprising the steps of:
 a) providing a visual performance level (VPL) value of at least one eye of the wearer, with the provision that prescription data (Rx) consisting of sphere, cylinder, axis, addition, prism are not defined as a visual performance level;
 b) providing a set of rules linking at least the visual performance level of step a) with at least one optical criterion chosen from at least one of the two following optical criteria groups:
  central vision optical criterion (CVOC) group consisting of prismatic deviation in central vision, ocular deviation, object visual field in central vision, image visual field in central vision, and magnification in central vision;
  peripheral vision optical criterion (PVOC) group consisting of pupil field ray deviation, object visual field in peripheral vision, image visual field in peripheral vision, prismatic deviation in peripheral vision, and magnification in peripheral vision; and
 c) calculating by computer means the physical and geometrical parameters of the personalized optical system that meets the prescription data of the wearer or selecting the personalized optical system in an optical systems data base comprising a plurality of optical systems that meet the prescription data of the wearer, so that to meet the set of rules of step b),
 wherein the rules of the set of rules refer to a link between at least a visual performance level and at least one optical criterion, and to a relationship between the said visual performance level and the said optical criterion.

2. The method according to claim 1, wherein rules of the set of rules of step b) are chosen within the list consisting of:
 providing a desired target value for at least a chosen optical criterion as a function of the value of the visual performance level value of step a);
 providing an equality or an inequality equation or a relationship between target values of the same optical criteria evaluated over at least two evaluation zones as a function of the value of the visual performance level value of step a); and
 providing a trend relationship between at least two chosen optical criteria as a function of the value of the visual performance level value of step a).

3. The method according to claim 2, wherein the visual performance level (VPL) of step a) is selected in the list of visual performances levels consisting of a sub-list of visual acuity performances, a sub-list of contrast sensitivity performances, a sub-list of visual space perception performance, a sub-list of reading performance, a sub-list of colour perception performance, a sub-list of self-reported visual performance, or a combination of at least two of said performances.

4. The method according to claim 3,
 wherein the sub-list of visual acuity performances consists of central visual acuity, peripheral visual acuity, dynamic visual acuity, each of said visual acuity being measured either according to monocular or to binocular vision and to either photopic or mesopic or scotopic vision conditions, or a combination of at least two of said visual acuity performances; and/or
 wherein the sub-list of contrast sensitivity performances consists of spatial contrast sensitivity, time contrast sensitivity, or a combination of said contrast sensitivity performances measured either according to monocular or to binocular vision and to either photopic or mesopic or scotopic vision conditions; and/or
 wherein the sub-list of "visual space perception" performances consists of distance perception acuteness, stereo acuity, aniseikonia measurement, moving object speed perception, visual field, being measured either photopic or mesopic or scotopic vision conditions, or a combination of at least two of said space perception performances; and/or
 wherein the sub-list of "reading performances" consists of reading rate performance, reading comprehension performance, word identification performance, being measured either according to monocular or to binocular vision and to either photopic or mesopic or scotopic vision conditions, or a combination of at least two of said reading performances; and/or
 wherein the sub-list of "color perception performances" consists of hue discrimination, saturation discrimination, brightness discrimination measured either according to monocular or to binocular vision and to either photopic or mesopic or scotopic vision conditions, or a combination of at least two of said color perception performances; and/or
 wherein the sub-list of "self-reported visual performances" consists of visual related quality of life questionnaires as national eye institute (NEI) visual functioning questionnaire or developed questionnaire on subjective visual performance during defined activities and/or defined conditions or a unique question about self-reported visual performances.

5. The method according to claim 2, wherein the visual performance levels are selected and wherein a global visual performance scale is defined.

6. The method according to claim 1, wherein the optical system is selected in optical systems data base and wherein all the optical systems of the optical systems data base have been calculating previously taking into account at least a same focalisation criterion over an evaluation zone according to at least a gaze direction.

7. The method according to claim 1 wherein the physical and geometrical parameters of step c) are calculated by computer means with an optimization method wherein at least a focalisation criterion (a) over an evaluation zone according to at least a gaze direction is taken into account to implement the calculation.

8. The method according to claim 6, wherein the focalisation criterion is selected in the list consisting of optical power, astigmatism, high order aberration (HOA), strehl ratio, root means square (RMS), drop in acuity or contrast.

9. The method according to claim 1, wherein the personalized optical system characterizing a progressive addition spectacle lens wherein the front and the back surfaces may be progressive or regressive addition surfaces and wherein the geometrical factor Q=ADDF/ADD is a parameter used to meet the set of rules according to step c), ADDF being the addition of the front surface and ADD being the optical addition of the lens.

10. The method according to claim 1 wherein the personalized optical system characterises a progressive addition spectacle lens and wherein the "base curve" of the spectacle ophthalmic lens is a parameter used to meet the set of rules according to step c).

11. The method according to claim 1, wherein the personalized optical system characterises a progressive addition spectacle lens and wherein refractive index is a physical parameter used to meet the set of rules of step b) according to step c).

12. The method of claim 11,
wherein the visual performance level of step a) is chosen in the sub-list of visual acuity performance,
wherein an optical criterion of step b) is chosen within the visual field list consisting of object visual field in central vision, image visual field in central vision, object visual field in peripheral vision, image visual field in peripheral vision and another optical criterion of step b) is chosen within the magnification list consisting of magnification in central vision, magnification in peripheral vision, and
wherein the rule linking the preceding visual performance level and the two preceding optical criteria is a trend relationship where the higher is the visual acuity performance level of the eye of the wearer, the higher is the value of the optical criterion chosen in the visual field list, and that respectively the lower is the visual acuity performance level of the eye of the wearer, the higher is the value of the optical criterion chosen in the magnification list.

13. A method for manufacturing a spectacle ophthalmic lens for a wearer, the method comprising the steps of:
aa) providing the physical and geometrical parameters of a personalized optical system according to claim 1;
bb) providing a lens substrate; and
cc) manufacturing the spectacle ophthalmic lens according to the parameters of step aa).

14. A non-transitory computer program product comprising one or more stored sequence of instructions that is accessible to a processor and which, when executed by the processor, causes the processor to carry out the step c) of claim 1.

15. A non-transitory computer-readable medium storing one or more sequences of instructions of the non-transitory computer program product of claim 14.

* * * * *